United States Patent [19]

Kocache et al.

[11] Patent Number: 4,794,334
[45] Date of Patent: Dec. 27, 1988

[54] PARAMAGNETIC GAS MEASURING APPARATUS

[75] Inventors: Riad M. A. Kocache; Danny F. Holman, both of Crowborough, England

[73] Assignee: Servomex, Ltd., Crowborough, England

[21] Appl. No.: 2,601
[22] PCT Filed: May 7, 1986
[86] PCT No.: PCT/GB86/00244
§ 371 Date: Dec. 11, 1986
§ 102(e) Date: Dec. 11, 1986
[87] PCT Pub. No.: WO86/06837
PCT Pub. Date: Nov. 20, 1986

[30] Foreign Application Priority Data

May 8, 1985 [GB] United Kingdom ............... 8511618

[51] Int. Cl.$^4$ .................... G01N 27/74; G01R 33/12
[52] U.S. Cl. ..................................... 324/204; 73/27 A
[58] Field of Search ............... 324/204; 73/23, 27 A, 73/861, 27 R

[56] References Cited

U.S. PATENT DOCUMENTS 2,416,344 2/1947 Pauling .
2,962,656 11/1960 Munday .......................... 324/204 X
3,026,472 3/1962 Greene et al. ...................... 324/204
3,292,421 12/1966 Meyer .
3,612,991 10/1971 Greene ............................... 324/204

FOREIGN PATENT DOCUMENTS 1031737 6/1953 France .
2096785 2/1972 France .

Primary Examiner—Gerard R. Strecker
Assistant Examiner—Warren S. Edmonds
Attorney, Agent, or Firm—Marjama & Pincelli

[57] ABSTRACT

Gas testing apparatus comprises a gas chamber wherein a test body surrounded by a single turn electrical conductor is suspended by a metal strip in a non-uniform and non-symmetrical magnetic field which is formulated by especially shaped pole pieces which could, in one form, by permanent magnets. The test body is deflected from the initial position it takes when a reference gas is in the cell, by the admittance of a gas mixture of which is paramagnetic gas is one constituent. The deflection is sensed by an optical system comprising a light source, a mirror on the test body and a pair of photocells. The output of the photocells feeds an amplifier system, which in turn feeds the single turn coil by a current of an adequate value such that it stops the test body from moving from its initial position and hence is proportional to the partial pressure of the paramagnetic gas in the sample. The effect of the gas entering the chamber and influencing the test body is minimized by the especial design of the gas inlet, outlet and route within the chamber. The cell is rendered gas tight by hermetic and mechanical seals rather than by the use of adhesive.

16 Claims, 6 Drawing Sheets

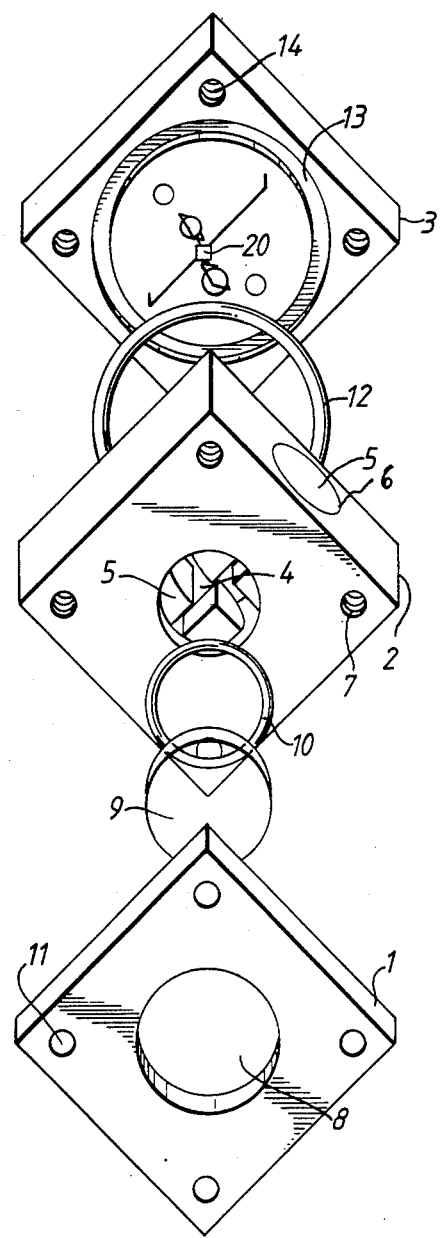
FIG. 1.
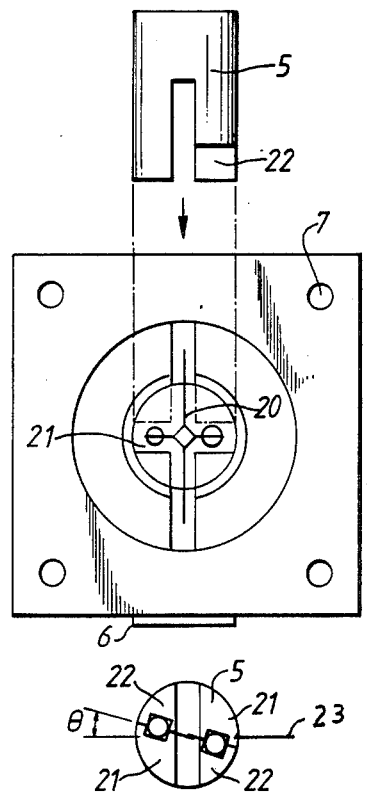
FIG. 2A.
FIG. 2B.

PARAMAGNETIC GAS MEASURING APPARATUS

The invention relates to devices that detect gases which have a strong paramagnetic susceptibility, such as oxygen, relative to most other common gases which have a weak diamagnetic susceptibility.

Such devices utilise a test body such as a dumb-bell suspended in a strong non-uniform magnetic field by a metallic strip and have a mirror on the test body which is part of an optical lever comprising a light source and a pair of opposing photocells. This optical system enables detection of the slightest movement of the test body from a reference position, when a reference gas such a nitrogen is present in the chamber displaced by a sample gas containing a constituent which is paramagnetic such as oxygen. The movement of the test body is inhibited by arranging a single turn coil round it and energising it by a current derived from an amplifier network which is driven from the photocells. The value of the current required to keep the test body in its initial reference position against the magnetic force induced by the paramagnetic component in the sample gas is linearly proportional to the partial pressure of that gas in the cell chamber.

Devices based on this principle have been described in U.K. Pat. Nos. 703,240 and 746,778 where the test body is made of quartz spheres filled with nitrogen. The dumb-bell, the mirror, the single turn coil: that is the components of the test body; are usually cemented together by adhesives such as an epoxy resin. The pole pieces and other cell components are also cemented together. The cell chamber is sealed using an epoxy resin.

The test body/optical lever system is very sensitive and thus can detect the small forces produced by the impingement of the incoming gas sample on it. This introduces noise into the measurement.

This problem was partially alleviated by adopting the design described in UK Pat. No. 829,444. This required however, in addition to the especially designed nozzles, an accurate and elaborate process of testing the induced flow errors, adjusting the angle of the nozzles and so on till the required performance is met. The inlet pipes had to be sealed gas tight with epoxy resin and keep their set position.

The deterioration of the epoxy resins used as cements and for gas tight seals, due to the presence of corrosive gases, solvent vapours and water vapour in the sample gas, results in gas leaks, output signal drift and changes in the temperature coefficient and sometimes in the collapse of the test body.

In an attempt to reduce this, UK Pat. No. 1,366,227 describes a test body which is assembled without the use of cements. Despite the great improvements brought by this design, the need to seal the cell and the inlet and outlet pipes gas tight with epoxy, the need to set and test the angle of the test body relative to the pole pieces axis so as to achieve workable spread in cell parameters, and the need to lock the test body at that angle with cement, left a large number of problems untackled.

From one aspect, the present application provides a cell structure which excludes the use of cements and epoxy. Preferably, a gas flow regime is provided which requires no setting of the gas pipes and whereby flow errors are minimal.

From another aspect, the present invention provides specially designed pole pieces which enables the replacement of the soft magnetic material used under normal conditions by a strong magnetic material if an integral magnet construction is required.

From a still further aspect, the present invention provides specially designed pole pieces the shape of the magnetic field which they produce ensures one equilibrium position only and produces a narrow spread in the initial position for the normal manufacturing spread in test bodies.

The present invention provides gas testing apparatus comprising a main body provided with a chamber, a hole extending from a first surface of the main body into the chamber, a test body located for movement in the chamber, means for permiting test gas to flow through said chamber, and means for applying a magnetic field to said test body in said chamber, characterised in that a front plate is provided arranged to be mechanically fixed to said first surface of the main body and provided with a window giving access to said hole, and in that a mechanical seal is provided between the front plate and said first surface.

In order that the present invention be more readily understood embodiments thereof will now be described by way of example with reference to the accompanying drawings, in which:

FIG. 1 is an exploded perspective view of a device according to a first embodiment of the present invention;

FIG. 2A is a front view of a part of the device shown in FIG. 1 with one pole piece separated for clarity;

FIG. 2B is a bottom view of the pole piece of FIG. 2A;

Figure 6A:
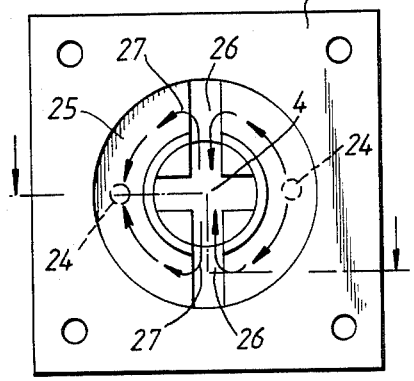
Figure 6B:
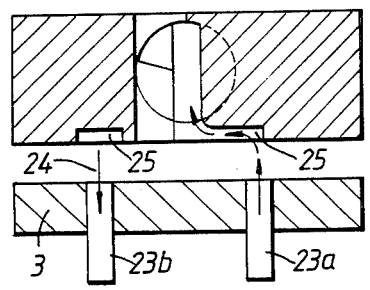
Figure 7:
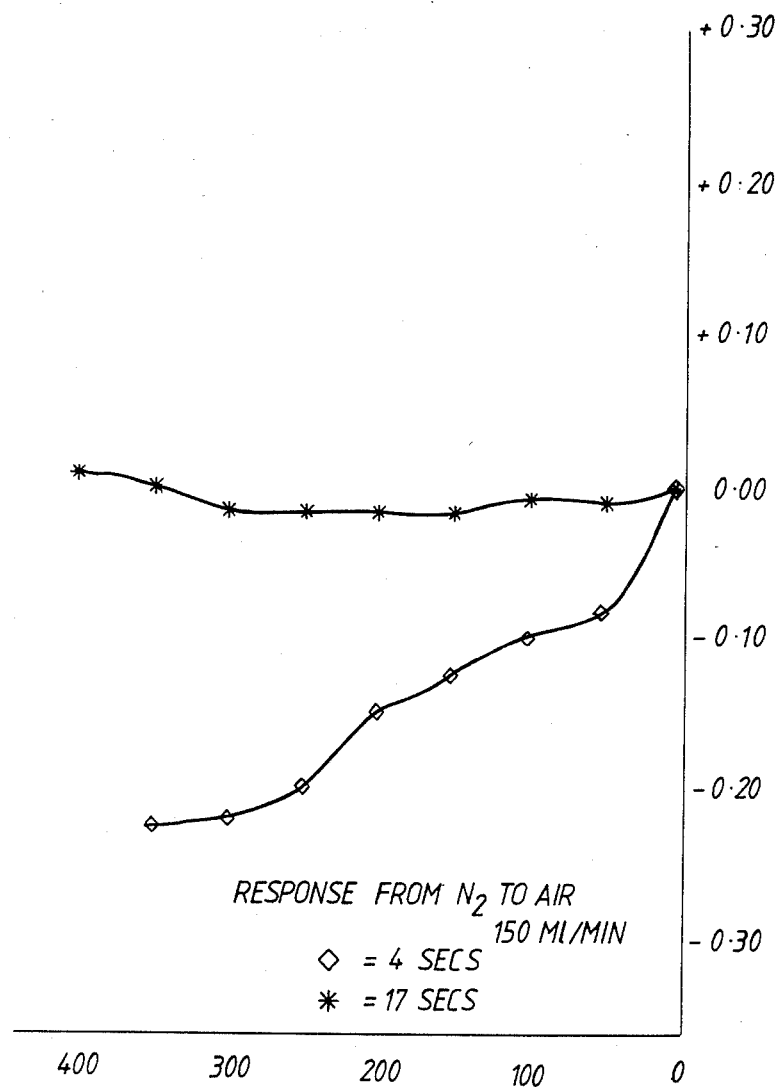
Figure 8:
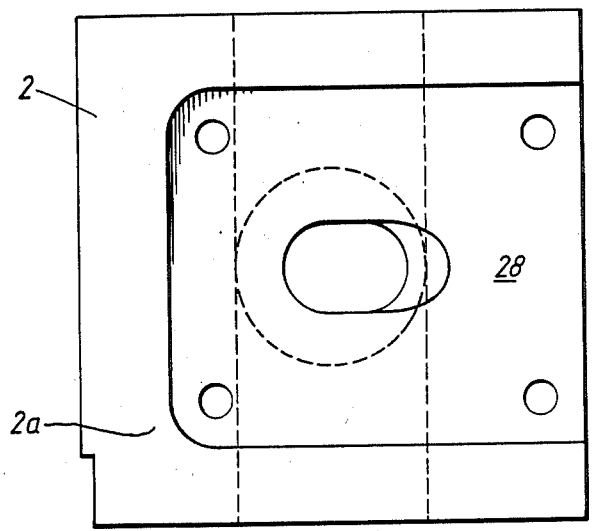
Figure 9:
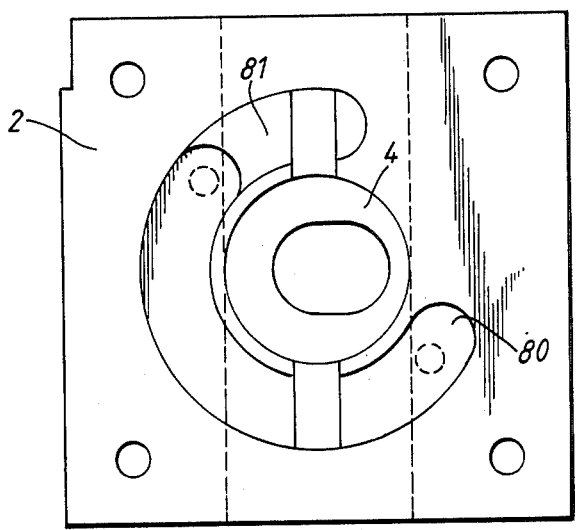
Figure 10:
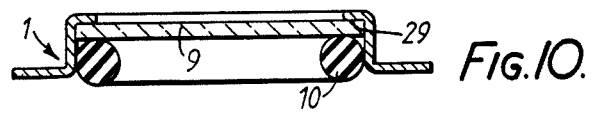
Figure 11:
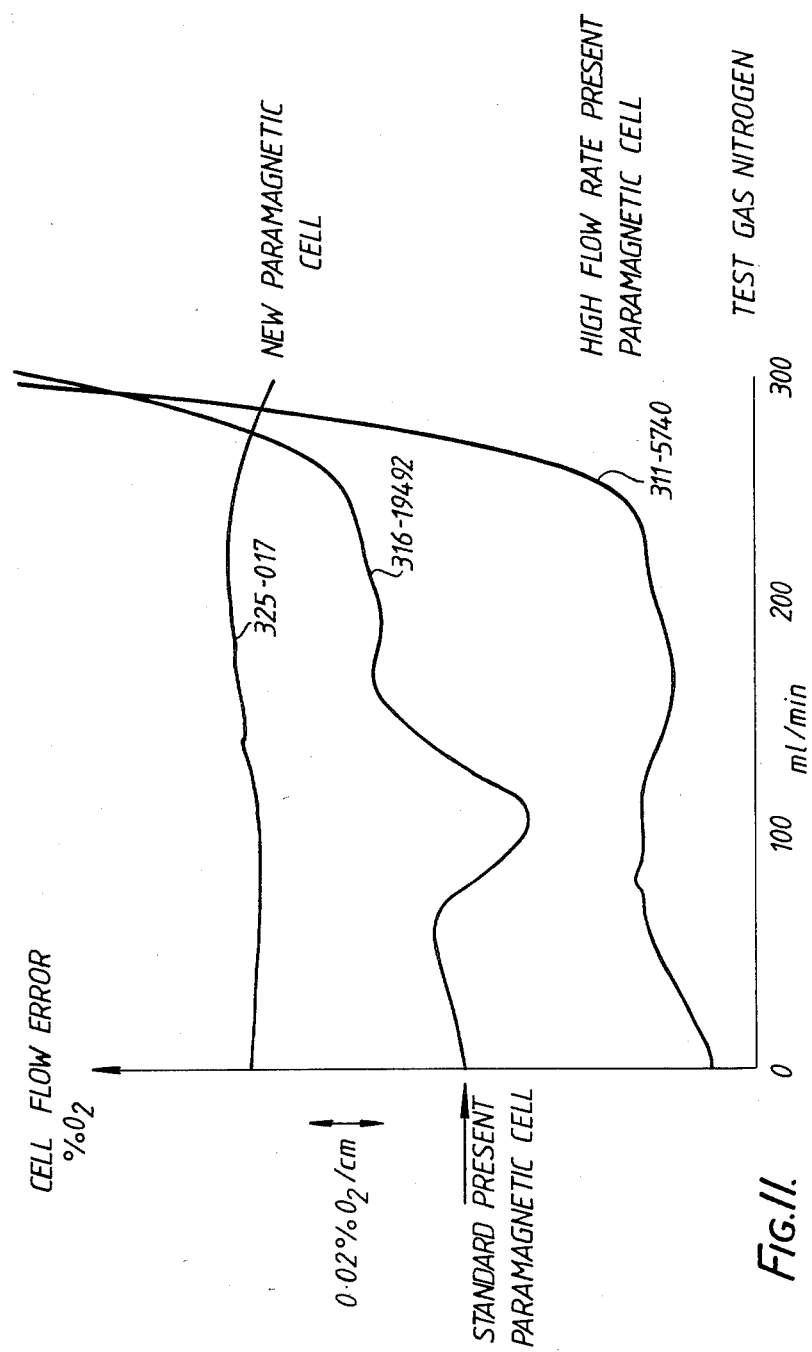

FIGS. 6A and 6B respectively show front and side views of parts of the device shown in FIG. 1 for explaining gas flows in the device;

FIG. 7 is a graph for explaining adjustment of gas flow paths;

FIG. 8 shows a front view of a modified main body portion used in a second embodiment of the present invention;

FIG. 9 shows a back view of the main body portion shown in FIG. 8;

FIG. 10 shows a crossectional view of a modified front used in the second embodiment of the present invention; and FIG. 11 shows a graph of cell flow error versus flow rate for comparing a flow cell according to the second embodiment with two different previously proposed flow cells.

The device structure is outlined in FIG. 1. It comprises three main elements. A front (1), a main body (2), and a back (3). The main body (2) provides a main gas chamber (4) to which sample gas is admitted.

The front (1) provides a means by which an optical source can be shone onto the mirror on the test body (20) which reflects the light back through the same means; this being an aperture cut in the metal (8) which is filled with an appropriate glass window (9). The front is rendered gas tight by the use of an 'O' ring (10) and four fixing screw (11) inserted in holes, which pull the front into the main body which is provided with appropriately threaded holes (7).

The back (3) is secured and sealed in a similar fashion by an 'O' ring (12) that is positioned in the correct position by a groove (13) in the cell back (3). This is secured gas tight by four screws going through holes (14) to appropriately threaded holes in the body.

Figure 3:
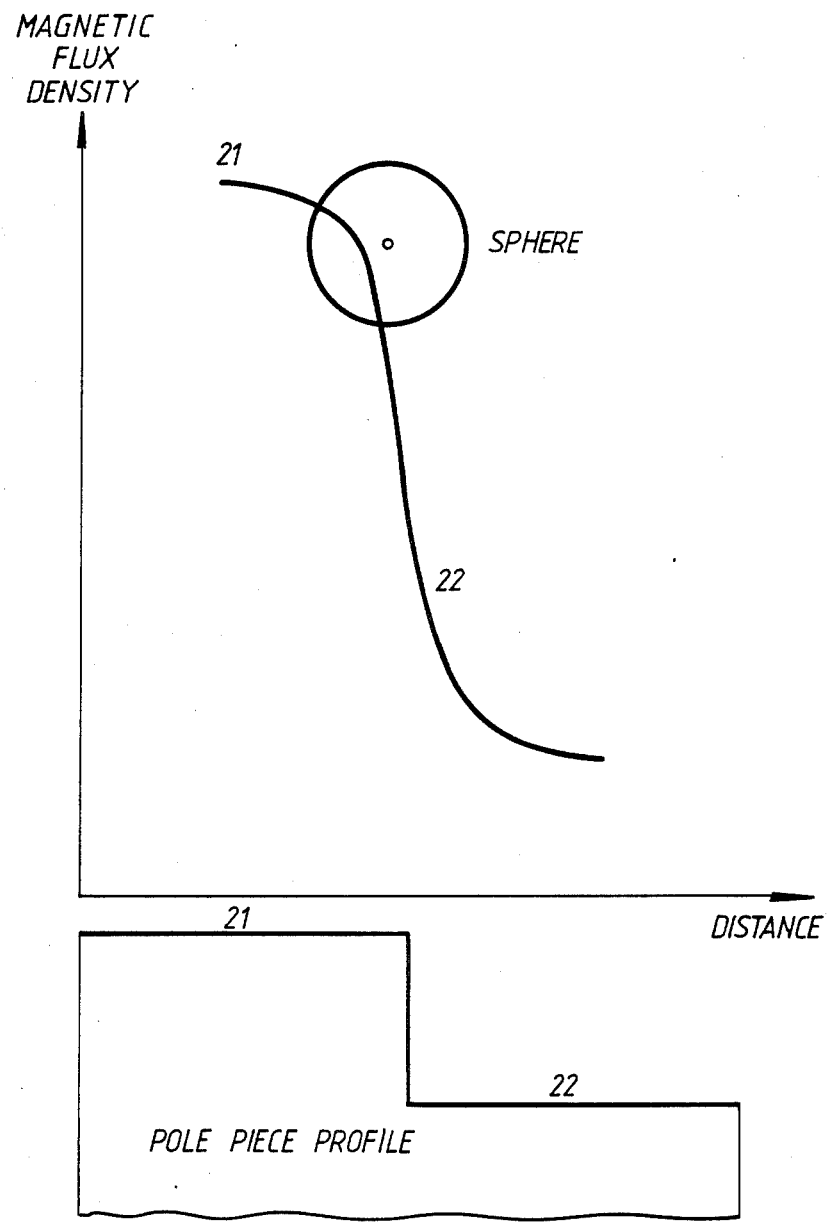
FIG. 3 is a diagram for explaining the operation of the device.

A test body (20) occupies a central position inside the chamber (4) along a vertical axis, and a slightly biased position in relation to the non-uniform and non-symmetrical magnetic field produced by the especial shape of pole pieces (5) positioned inside the chamber (4). The pole pieces (5) are normally made from a soft magnetic material and are rendered resistant to corrosive gases by a coating of nickel or any other material compatible with the chemical resistive properties of the body, the front and the back, (e.g. 316 stainless steel). The method of attachment of the pole pieces to the main body is by vacuum brasing or any other suitable technique such as electron beam welding, which forms a gas tight seal (6). FIG. 2A is a front view of the main body which clarifies this further. The pole pieces (5) define a first area (21) of a strong magnetic field where the upper pole piece is parallel to the lower one separated by a small gap that allows the test body (20) to swing freely within it. They also define a second area (22) where the gap is much larger and hence the magnetic field is much weaker. The two areas are not equal. The area with the small air gap continues beyond the line of midsymmetry (23) by an angle $\theta$. The value of this angle is related to the geometry of the optical, position-sensing system. The test body (20) is positioned to have the same angle $\theta$. This situates the back part of the spheres of the test body in the nearly uniform and very strong part of the magnetic field (21) and the front part in the highly non-uniform and very weak part of the magnetic field (22) as shown in FIG. 3.

Figure 4:
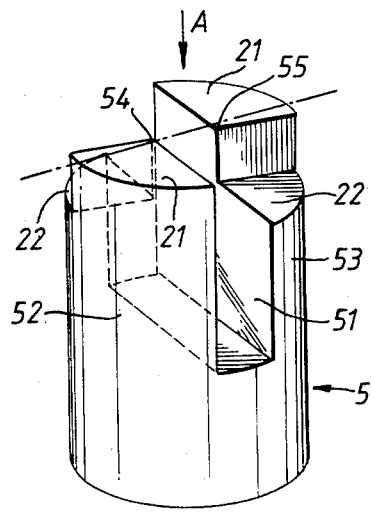
FIG. 4 is a perspective view of a pole piece used in the device of FIG. 1.

For completeness, the exact structure of one pole piece (5) will now be described with reference to FIG. 4 it being understood that the other pole piece is identical.

The pole piece (5) is generally cylindrical with a axial slot (51) extending some way down the length of the pole piece and two equal bifurcated legs (52,53). The free ends of the legs (52,53) are generally semicircular when viewed in the direction of arrow A. A sector shaped portion is then removed from each free end of the legs (52,53) but the apex (54) of the sector shaped portion in end of the leg (52) is displaced from the axis of the cylinder forming the pole piece on one side of the axis while the apex (55) of the sector shaped portion in the end of the leg (53) is displaced from the axis on the other side of the axis with respect to the apex (54).

The design of the pole pieces ensures:

An efficient use of driving permanent magnets (within which the cell is usually inserted);

The possibility of using very strong magnetic material instead of soft iron for the construction of the pole pieces (e.g. samarium magnets);

That the test body can only turn one way—away from the strong magnetic field—in the presence of a paramagnetic gas in the chamber (a single equilibrium position);

That the reference position of the test body in the presence of the reference gas (e.g. Nitrogen) has a narrow spread in relation to the manufacturing tolerances of the test-body component parts, in view of the fact that the magnetic field drops very sharply over a very small distance from a peak value to a very small value.

Figure 5A:
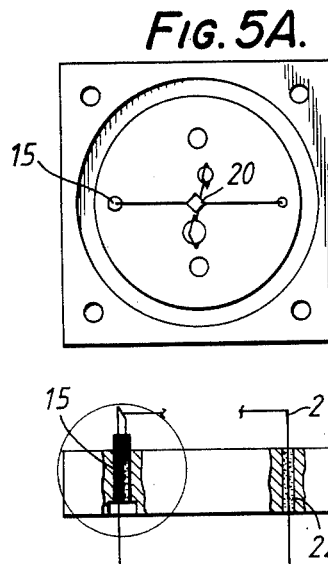
FIG. 5A is a front view of the back part of the device of FIG. 1.
Figure 5B:
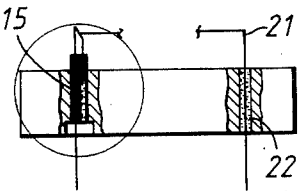
FIG. 5B is a side view of FIG. 5A partially broken away.
Figure 5C:
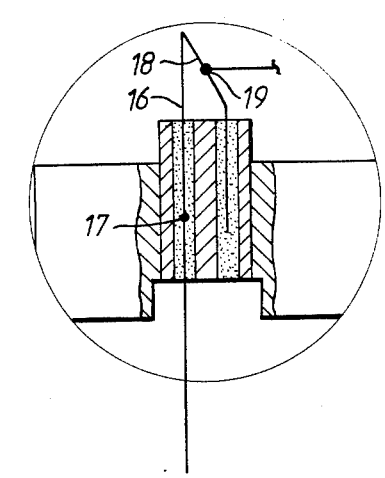
FIG. 5C is an enlarged view of the portion circled in FIG. 5B.

The test body (20) which is made as described in UK Pat. No. 1,366,227 is suspended in the appropriate position and under the right tension between a reference post (15) and a resilient post (21) as shown in FIGS. 5A, 5B and 5C. The post 15 comprises a twin bored ceramic insulator such as alumina with an appropriately shaped precious metal alloy wire (16) (e.g. Pt/Ir) which is joined at a point within the ceramic insulator to a normal electrical conductor (17). The wire is shaped such that its upper part (18) forms an angle $\theta$, similar to that of the pole piece (FIG. 2B). The wire is hermetically sealed to the insulator which is also hermetically sealed to the cell main body (2). The suspension strip coming from the test body is welded to the central part of the bar (19). The angle on the bar (19) ensures that the strip has the required bias angle so as to position the test body at the correct angle relative to the magnetic field. The other end of the strip is welded to the post (21). This is made of a precious metal alloy such at Pt/Ir, which acts as a spring. It is connected to an electrical conductor (22) and hermetically sealed to a ceramic insulator and to the cell back. High temperature glasses can be used to do this. The two electrical conductors emerging from the cell back provide a conductive path to the single turn coil round the test body.

Gas is admitted to the chamber and removed from it by two pipes (23a, 23b) as shown in FIGS. 6A anad 6B, symmetrically and diametrically placed in the back (3) of the cell. The pipes (23a, 23b) are silver soldered or vacuum brazed and arranged to emerge level with the surface of the cell back (24). A channel (25) of appropriate depth and circular path is machined in the back of the main body of the cell (2). The incoming gas impinges at right angles onto the floor of the groove and divides equally and flows through the channel. When it comes to the mid-section (upper and low mid-part of the cell), some of it continues to the opposite channel to leave the cell from the exit pipe (23b). Part of it also finds its way to the inner part of the cell (26) through internal slots which receive the suspension of the test body, thus exchanging the gas within the chamber. The flow path being along the mid-point and hence the length of the suspension of the test body does not exert a large torque on the test body (20), especially as the mechanism is more of a diffusion action. At the same time, there is a stream (27) being sucked out of the chamber and into the outlet channel.

By appropriately restricting half sections of the channel, conditions can be optimised so that either the cell is rendered flow insensitive for a large flow rate at the cost of a slow response time (FIG. 7) or improve the response time (by limited quarter restrictions) and hence reduce the region of low flow errors. These improvements and others will now be described in relation to a second embodiment of the present invention.

In the following description, the same reference numerals will be used for the same parts as in the first embodiment. Further, because the basic assembly is identical in both embodiments, only the differences between the two embodiments will be described. It is to be noted however, that any of the differences could be made individually to alter the first embodiment accordingly.

Referring now to FIGS. 8 and 9, these show front and back views of a modified form of main body (2). As will be seen from FIG. 8, the front surface (2a) of the main body now has a recessed area (28) which receives a modified front (1) as will be described in relation to FIG. 10. The recessing permits the front surface (2a) of the main body to act as a reference surface when positioning the cell in use.

The rear of the main body (2) has been modified to provide a different flow pattern of test gas to improve the cell flow error characteristics. The groove (25) of the previous embodiment has been replaced by a truncated groove (80) with the position of the inlet pipe (23a) and the outlet pipe (23b) being handed in broken lines. The pipes are still diametrically oppsite each other but are now moved off the centre line. The movement of the outlet pipe off the centre line does not affect its operation and it has been found that the groove (80) need not be complete. However, movement of the inlet pipe off the centre line would affect the gas flow conditions as it would be nearer one entrance to the inner part of the cell than the other. To compensate for this, the groove (80) between the inlet pipe and the rear of the two entrances is carefully dimensioned to equalise flows into the cell. This is achieved by having the floor of the groove (80) provided with a raised portion (81) over a predetermined length.

These alterations to the gas flow groove have resulted in an improved performance of the cell as shown by FIG. 11 where the new cell will be seen to have an almost flat response over a flow rate range from 0 to 300 ml/min.

A performance improvement can also be achieved by retaining the original positions of the inlet and outlet but by introducing the portion of reduced crosssectional area into a truncated groove.

Turning now to FIG. 10, the modified front (1) is smaller than the front surface (2a) of the main body (2) and is received in the recessed portion (28). The front (1) is formed to provide a recess (29) for receiving the window glass (9) and the O-ring (10). As before the front (1) is attached to the main body by screws and the O-ring mechanically sends the front opening into the main body through which the light beam from the external monitoring equipment is transmitted to and reflected from the test body.

It is possible to replace the pole pieces (5) by permanent magnets in which case the shape of each magnet may be slightly different to the shape of the pole pieces. It is preferred that rather than simply removing a small axial length of sector shaped material, each bifurcate leg will be formed as a sector shaped elongate permanent magnet derived by a cylindrical soft strong member. This saves material and weight and permits a portable test chamber.

I claim:

1. Gas testing apparatus comprising a main body provided with a chamber, a hole extending from a first surface of the main body into the chamber, a test body located for movement in the chamber, means for permitting test gas to flow through said chamber, and means for applying a magnetic field to said test body in said chamber, characterized in that a front plate is provided arranged to be mechanically fixed to said first surface of the main body and provided with a window giving access to said hole, a mechanical seal is provided between the front plate and said first surface, said hole extends through said chamber to a second surface of said main body, a back plate is mechanically affixed to said second surface, a mechanical seal is provided between said back plate and said second surface, said test body is mounted on a suspension provided on said back plate, said means for permitting gas to flow through said chamber comprises an inlet and an outlet passageway communicating with a groove in the second surface of the main body which groove in turn communicates with entrances to the chamber, said inlet and outlet passageways extend through the back plate to communicate with the groove such that gas passing through the inlet passageway impinges at right angles on to a wall of the groove to cause the gas flow to divide into two.

2. Apparatus according to claim 1, wherein the test body comprises a member mounted on a suspension and rotatable in said chamber, said suspension being located in said entrances to the chamber through which flows gas to be tested.

3. Apparatus according to claim 1, wherein the inlet and outlet passageways are diametrically opposite each other.

4. Apparatus according to claim 1, wherein the groove is circular.

5. Apparatus according to claim 1, wherein the groove is an incomplete circle.

6. Apparatus according to claim 5, wherein the inlet passageway is located closer to one entrance than to the other, and the groove is provided with a portion of restricted cross-sectional area between the inlet passageway and said one entrance.

7. Apparatus according to claim 1, wherein the back is fixed to the main body by screw threaded members.

8. Gas testing apparatus comprising a main body provided with a chamber, a hole extending from a first surface of the main body into the chamber, a test body located for movement in the chamber, means for permitting test gas to flow through said chamber, and means for applying a magnetic field to said test body in said chamber, characterized in that a front plate is provided arranged to be mechanically fixed to said first surface of the main body and provided with a window giving access to said hole, a mechanical seal is provided between the front plate and said first surface, said hole extends through said chamber to a second surface of said main body, a back plate is mechanically affixed to said second surface, a mechanical seal is provided between said back plate and said second surface, said test body is mounted on a suspension provided on said back plate, said means for permitting gas to flow through said chamber comprises an inlet and an outlet passageway communicating with a groove in the second surface of the main body which groove in turn communicates with entrances to the chamber, said inlet and outlet passageways extend through the back plate to communicate with the groove such that gas passing through the inlet passageway impinges at right angles on to a wall of the groove to cause the gas flow to divide into two said mechanical seals being elastomeric members.

9. Apparatus according to claim 8, wherein the elastomeric members are O-rings.

10. Gas testing apparatus comprising a main body provided with a chamber, a hole extending from a first surface of the main body into the chamber, a test body located for movement in the chamber, means for permitting test gas to flow through said chamber, and means for applying a magnetic field to said test body in said chamber, characterized in that a front plate is provided arranged to be mechanically fixed to said first surface of the main body and provided with a window giving access to said hole, a mechanical seal is provided between the front plate and said first surfce, said hole extends through said chamber to a second surface of said main body, a back plate is mechanically affixed to said second surface, a mechanical seal is provided between said back plate and said second surface, said test body is mounted on a suspension provided on said back plate, said means for permitting gas to flow through said chamber comprises an inlet and an outlet passageway communicating with a groove in the second surface of the main body which groove in turn commuicates with entrances to the chamber, said inlet and outlet passageways extend through the back plate to communicate with the groove such that gas passing through the inlet passageway impinges at right angles on to a wall of the groove to cause the gas flow to divide into two, said means for applying a magnetic field to said first body in said chamber comprises a pair of members of a magnetic material mounted in bores extending into the chamber at right angles to said hole, the members being sealed into said bore without the use of adhesives.

11. Apparatus according to claim 10, wherein the members are pole pieces.

12. Apparatus according to claim 11, wherein the pole pieces are each cylindrical with an axially extending slot cut into one end to form two legs, the free end face of each leg having a sector shaped piece of material removed therefrom with the removed sectors diametrically opposed to each other, and the members being mounted with their respective sector shaped portions in register with each other.

13. Apparatus according to claim 10, wherein the members are made of permanent magnets.

14. Apparatus according to claim 10, wherein the front is shaped to provide a recess for a window glass.

15. Apparatus according to claim 14, wherein the recess in the front accommodates the window glass and an O-ring.

16. Apparatus according to claim 10, wherein the front is fixed to the main body by screw threaded members.

* * * * *